US006286346B1

(12) United States Patent
Hocken, Jr. et al.

(10) Patent No.: US 6,286,346 B1
(45) Date of Patent: *Sep. 11, 2001

(54) INTERRUPTABLE MULTIPLY AND/OR DIVIDE OPERATIONS FOR USE WITH AN INTERRUPT IN A MEDICAL DEVICE PROCESSOR

(75) Inventors: Robert W. Hocken, Jr., Scottsdale; Kevin K. Walsh, Glendale, both of AZ (US); Jeffrey D. Wilkinson, Vadnais Heights, MN (US)

(73) Assignee: Medtronic, Inc., Minneapolis, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/070,407

(22) Filed: Apr. 30, 1998

(51) Int. Cl.[7] .................................................. G06F 9/302
(52) U.S. Cl. .......................... 70/260; 710/266; 710/267; 712/221; 708/627; 708/655
(58) Field of Search ................................ 708/208, 503, 708/504, 620, 650, 627, 655; 711/103; 710/262, 267, 268, 269, 48, 260, 266; 712/221

(56) References Cited

U.S. PATENT DOCUMENTS

| 4,238,833 | 12/1980 | Ghest et al. | 708/628 |
|---|---|---|---|
| 4,337,519 | 6/1982 | Nishimoto | 708/629 |
| 4,665,500 | 5/1987 | Poland | 708/628 |
| 4,831,571 | * | 5/1989 | Tokumaru | 708/209 |
| 5,241,492 | | 8/1993 | Girardeau, Jr. | 708/523 |
| 5,287,523 | * | 2/1994 | Allison et al. | 710/50 |
| 5,349,667 | * | 9/1994 | Kaneko | 710/267 |
| 5,507,001 | * | 4/1996 | Nishikawa | 710/5 |
| 5,576,982 | * | 11/1996 | Wu et al. | 708/211 |
| 5,896,305 | * | 4/1999 | Bosshart et al. | 708/209 |
| 5,951,685 | * | 9/1999 | Stancil | 713/2 |

* cited by examiner

Primary Examiner—Kenneth S. Kim
(74) Attorney, Agent, or Firm—Girma Wolde-Michael; Thomas F. Woods

(57) ABSTRACT

A method and apparatus including conditional add and conditional add/subtract instructions are provided for use in the instruction set of a medical device instruction processor. More specifically, the conditional add and add/subtract instructions are provided to add two operands if a predetermined condition is satisfied within the instruction processor hardware. Additionally, the conditional add/subtract instruction may be used to subtract one operand from another operand if the predetermined condition is not satisfied. These instructions are adapted for use in implementing an efficient, interruptible, firmware-controlled multiplication or division mechanism. The inventive system allows multiplication or division operations to be interrupted at various intermediate points during the multiplication or division operation to thereby reducing interrupt latency.

31 Claims, 8 Drawing Sheets

INTERRUPTABLE MULTIPLY AND/OR DIVIDE OPERATIONS FOR USE WITH AN INTERRUPT IN A MEDICAL DEVICE PROCESSOR

FIELD OF THE INVENTION

The present invention relates generally to data processors of medical devices. More particularly, the present invention pertains to methods and apparatus for performing multiply and divide operations by such processors.

BACKGROUND OF THE INVENTION

Microcomputers are sophisticated, general purpose logic devices which can be programmed to perform a wide variety of useful functions in various devices such as communication equipment, medical devices, and other apparatus such as educational devices, household appliances, consumer goods, and the like. Generally, an entire spectrum of microcomputers is available in the marketplace. In particular medical devices, such as implantable devices, e.g., implantable pacemakers and defibrillators, data processors should have maximum processing capability. However, such maximum processing capability must be weighed against the need for low power requirements. For example, such low power processor designs are available from Motorola under the 6811 C trade designation, from Intel under the 8052 trade designation, etc.

The architecture of a data processor pertains to the various component parts of the processor and interconnection therebetween. A data processor typically uses a central processing unit (CPU) as the controller for the other component parts. The CPU is generally interfaced to or includes an arithmetic logic unit (ALU).

The ALU is a device which accepts data and performs certain operations thereon. These operations are generally grouped as either arithmetic or logical in nature. The CPU controls the data delivered to and selects the operation of the ALU which performs an operation on the actual bit structure of the data so as to implement the desired functions. The data is stored within the CPU or alternatively in other accessible memory in the form of data words. The length of the data word is used to describe the data processor since the length is directly related to the precision of the data processor. A 16-bit data word processor has the capability of defining the number with much more precision than a 4-bit data word processor.

The data processor accepts data, manipulates it using the ALU, and places it in an inactive state such as retained in a memory until the data is later needed. Communication channels electrically connect the CPU with memory. The CPU responds to instructions stored as machine language. Machine language is instructions coded into a word, generally, of the same length as the data word. The instructions are stored in the memory and are retrieved by the CPU.

Since the memory contains both data and instructions for the data processor, some flag or signal is used to keep the processor from confusing what it is receiving from the memory. For example, an architecture may provide for flagging of the data and instructions stored in memory. Such an arrangement allows the data processor to perform tasks according to prioritization. When a high priority task interrupts a lower priority task, then the lower priority task operation is halted and the data in the processor and the status information relating to the lower task is stored in a memory until the higher priority task is completed. Once completed, the process is set at the state where the lower priority task was interrupted.

The throughput of any given data processor is a function of, among other things, the number of machine cycles required to execute a given set of instructions. In the course of designing any computer system, and in particular a microcomputer, a set of instructions is selected which will provide the anticipated requirements for the projected market in which the computer system is to be used, e.g., a low power processing unit for medical devices. Generally, the processor executes each instruction as a sequence of machine cycles, with the more complex instructions consuming a greater number of machine cycles. The operation of internal registers and gating circuitry of the data processor is synchronized by a master clock signal applied to the data processor. During a basic clock cycle, also commonly known as the machine cycle, a number of internal processor related operations may take place simultaneously, including the transfer of digital information from a bus to a register or vice-versa between certain registers, from an address or data buffer to a bus or vice-versa and so forth, the individual conductors of a bus may each be set to the predetermined logic level, or the contents of a register may be set to a predetermined logic level. The more processor operations occurring within an individual machine cycle, the fewer the number of machine cycles required for the execution of a particular instruction.

Various techniques have been used for implementing multiply and/or divide functions in data processors. For example, conventional microprocessors have implemented multiply and divide operations using microcode or using firmware. However, implementation of such operations in conventional manners has resulted in less than adequate processing capabilities, particularly for low power data processors. For example, with regard to microcode (i.e., an internal program which executes external instructions provided by the user), the microcode is generally stored in an internal memory array. Generally, program counter logic receives an external instruction and then accesses a microcode entry or jumps to a microcode routine to execute the external instruction, e.g., a multiply or divide instruction. The program counter logic may include mechanisms for waits, conditional jumps, and sequencing of instructions stored in the microcode (also known as microinstructions). The data processor stores data in internal registers and moves data internally using data paths.

When the program counter logic accesses the microcode, it provides a data element known as a microinstruction, which includes fields defining hardware of the processor to be enabled, data to be moved, etc. The fields are encoded, and a decoder is necessary to convert the field into control signals which enable and disable the hardware for operation. When the user provides an external arithmetic instruction, e.g., a multiply or a divide instruction, the microcode causes data to be moved via the internal data paths to the arithmetic hardware and activates appropriate portions of the hardware to perform the external instruction.

For example, when the microcode provides a multiply microinstruction, fields in the microinstruction cause the operands to move via the internal data paths and to be provided as inputs to a hardware multiplier. Conventional hardware multipliers, such as booth multipliers and array multipliers, are known to provide high speed operation and are frequently used in processor design. However, such high speed multipliers operate with unacceptably long delays for servicing interrupts for the data processor. Further, such multipliers also consume a lot of power and thus present limitations to the operation of data processors which are required to operate in low power environments, e.g., implantable devices. In addition, a significant amount of hardware is required to implement the algorithm resulting in increased die size. In other words, in a low power processor which generally operates at a low clock rate, it is unacceptable to have an instruction like a multiply or divide which executes for many sequential clock cycles without permitting interruption. Such is the case with a microcode/hardware implementation of a multiply and/or divide operation.

With regard to a firmware implementation of a multiplication or division, such a delay problem in servicing interrupts is not problematic. The firmware implementation can be interrupted at virtually any point in the multiplication or division operation. However, in conventional firmware implementations of a multiply or a divide operation, generally either a large number of instructions are required for performing such a multiply or divide operation or a smaller number of instructions are needed which loop over and over but which causes the CPU to spend more time managing the loop, rather than performing the multiply/divide function. For example, in one case 64 instructions are necessary to perform a multiply or divide operation on a 16-bit processor, and 96 instructions are generally required for such an operation on an 8-bit processor. Such a large number of instructions are undesirable. The number of instructions or loops should be minimized so as to minimize the number of machine cycles utilized during a particular multiplication or division operation. With reduction in the number of such machine cycles, device longevity is increased and lower power consumption is achieved.

Further, in low power processor designs, especially for use in implantable devices, chip size reduction is also of importance. Generally, any reduction in chip space used is desirable.

Various implementations of multiply and divide functions are known in the art, some examples of which may be found in the issued U.S. Patents listed in Table 1 below.

TABLE 1

| U.S. Pat. No. | Inventor(s) | Issue Date |
| --- | --- | --- |
| 5,241,492 | Girardeau, Jr. | 31 August 1993 |
| 4,337,519 | Nishimoto | 29 June 1982 |
| 4,238,833 | Ghest, et al. | 9 December 1980 |
| 4,665,500 | Poland | 12 May 1987 |

All patents listed in Table 1 hereinabove are hereby incorporated by reference herein in their respective entireties. As those of ordinary skill in the art will appreciate readily upon reading the Summary of the Invention, the Detailed Description of the Embodiments, and the claims set forth below, many of the devices and methods disclosed in the patents of Table 1 may be modified advantageously by using the teachings of the present invention.

SUMMARY OF THE INVENTION

The present invention has certain objects. That is, various embodiments of the present invention provide solutions to one or more problems existing in the prior art with respect to multiply and/or divide operations in data processors, particularly low power data processors. Such problems include unacceptably long delays in the servicing of interrupts for various multiplication and/or division operation implementations, undesirably large amounts of instructions for implementation of multiply or divide operations (e.g., firmware implementations resulting in decreased device longevity), and use of precious semiconductor chip area for implementation of such multiply and divide functions. Various embodiments of the present invention have the object of solving at least one of the foregoing problems. While firmware implementations have been able to solve the problems of unacceptably long delays in servicing interrupts, such implementations have generally used an undesirably large cycle count to perform such operations.

In comparison to known implementations of multiply and divide operations for data processors, various embodiments of the present invention may provide one or more of the following advantages: providing interruptible integer multiply and/or divide operations; enabling low power interruptible multiply and/or divide operations; provide for decreased chip space use to decrease device size, such as implantable device size; increase device longevity as a result of decreased cycles used for performing multiply and/or divide operations; and providing increased speed of execution of such integer multiply and/or divide operations relative to other firmware implementations.

Some embodiments of the invention include one or more of the following features: a conditional add instruction; a conditional add/subtract instruction; a rotate instruction; a shift instruction; executing a conditional add instruction wherein an addressed operand is added to the contents of an accumulator and then saved back to the accumulator if a conditional bit is set, however, if the conditional bit is not set, then going to the next instruction; combining an accumulator and a shift path register to form a shift path for execution of a shift instruction; combining a carry bit, an accumulator, and a shift path register to form the shift path; shifting bits of the shift path one bit position to the right (e.g., a carry bit is shifted into the most significant bit of the accumulator and the least significant bit of the accumulator is shifted into the most significant bit of another register); combining an accumulator and a shift path register to form a shift path for use in execution of a rotate instruction; combining a carry bit, an accumulator, and a shift path register to form the shift path; rotating bits of the shift path left one bit position (e.g., the most significant bit of the accumulator is rotated into the carry bit and the carry bit is rotated into the least significant bit of another register); executing a conditional add/subtract instruction wherein an addressed operand is added to the content of an accumulator and then the result is saved back to the accumulator if a conditional bit is set; executing a conditional add/subtract instruction wherein an addressed operand is subtracted from the content of an accumulator and then the result is saved back to the accumulator if a conditional bit is not set; interrupting multiply and/or divide operations performed using conditional add, conditional add/subtract, rotate, and shift instructions.

DETAILED DESCRIPTION OF THE EMBODIMENTS

Figure 1:
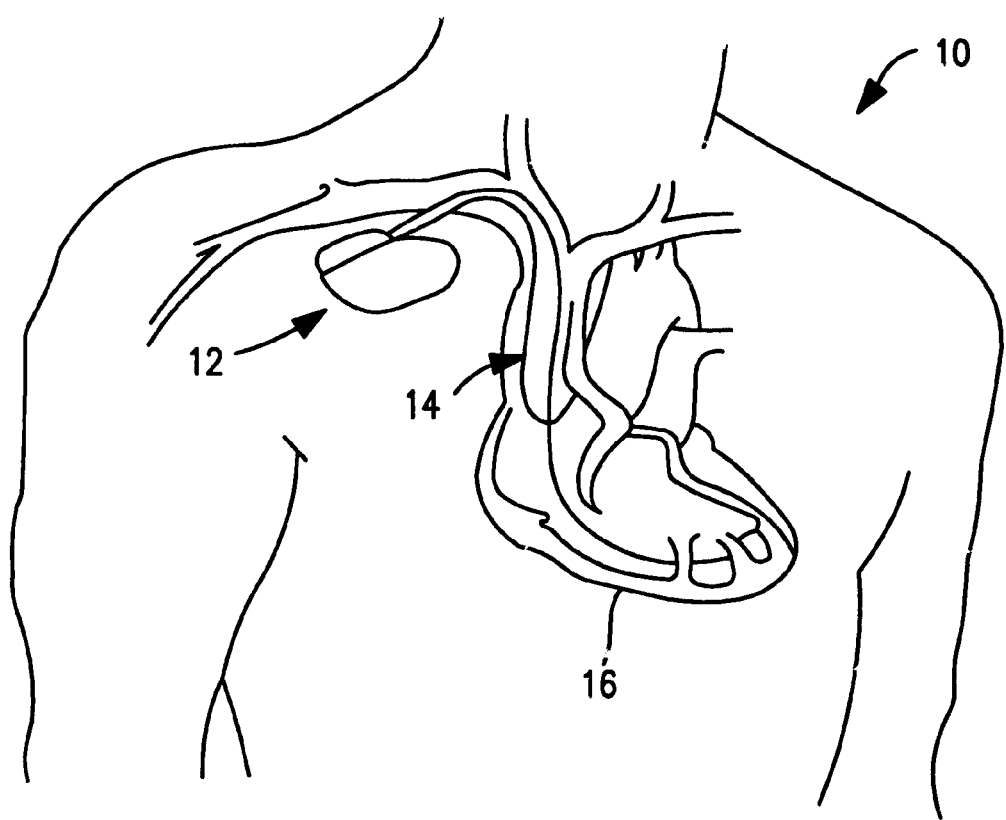
FIG. 1 shows an implantable medical device having a data processor according to the present invention implanted in a body.

FIG. 1 is a simplified schematic view of an implantable medical device 12 including a microprocessor according to the present invention implanted in a body 10 near a human heart 16. The implanted medical device 12 is electrically connected to the heart by leads 14. In the case where the implanted medical device 12 is a pacemaker, the leads 14 are pacing and sensing leads connected to the heart 16 from the implantable medical device 12. Such leads sense electrical signals attendant to the depolarization and repolarization of the heart 16 and provide pacing pulses for causing depolarization of cardiac tissue in the vicinity of the distal ends thereof. Implantable medical device 12 may be any implantable cardiac pacemaker such as those disclosed in U.S. Pat. No. 5,158,078 to Bennett et al., U.S. Pat. No. 5,312,453 to Shelton et al., or U.S. Pat. No. 5,144,949 to Olson, hereby incorporated herein by reference in their respective entireties.

Implantable medical device 12 may also be a pacemaker/cardioverter/defibrillator (PCD), one of which is further described below. The present invention may be practiced in conjunction with PCDs such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless, or U.S. Pat. No. 4,821,723 to Baker et al., all hereby incorporated herein by reference in their respective entireties. Those devices may be employed directly in conjunction with the present invention in that such devices employ a microprocessor performing multiply and/or divide operations according to the present invention.

Alternatively, implantable medical device 12 may be an implantable nerve stimulator or muscle stimulator such as those disclosed in U.S. Pat. No. 5,199,428 to Obel et al., U.S. Pat. No. 5,207,218 to Carpentier et al., or U.S. Pat. No. 5,330,507 to Schwartz, or an implantable monitoring device such as that disclosed in U.S. Pat. No. 5,331,966 issued to Bennet et al., all of which are hereby incorporated by reference herein in their respective entireties. The present invention is believed to find wide application to any form of implantable electrical device which incorporates a processor, and the present invention is believed to be particularly advantageous in those contexts where a low power processor is employed and desired. However, the present invention is equally applicable to other processors for other applications, e.g., communications, particularly where low power is desired.

In general, the implantable medical device includes a hermetically-sealed enclosure that may include various elements such as an electrochemical cell (e.g., a lithium battery), circuitry that controls device operations and records arrhythmic EGM episodes, telemetry transceiver antenna and circuit that receives downlinked telemetry commands from and transmits stored data in a telemetry uplink to an external programmer, etc. In accordance with the present invention, the device is a microcomputer-based system. However, it is to be understood that the present invention is not limited in scope to particular electronic features and operations of particular medical devices and that various devices may be employed in conjunction with a processor according to the present invention. Further, the present invention is not limited in scope to implantable medical devices including only a single microprocessor but may be applicable to devices including multiple processors as well.

Figure 2A:
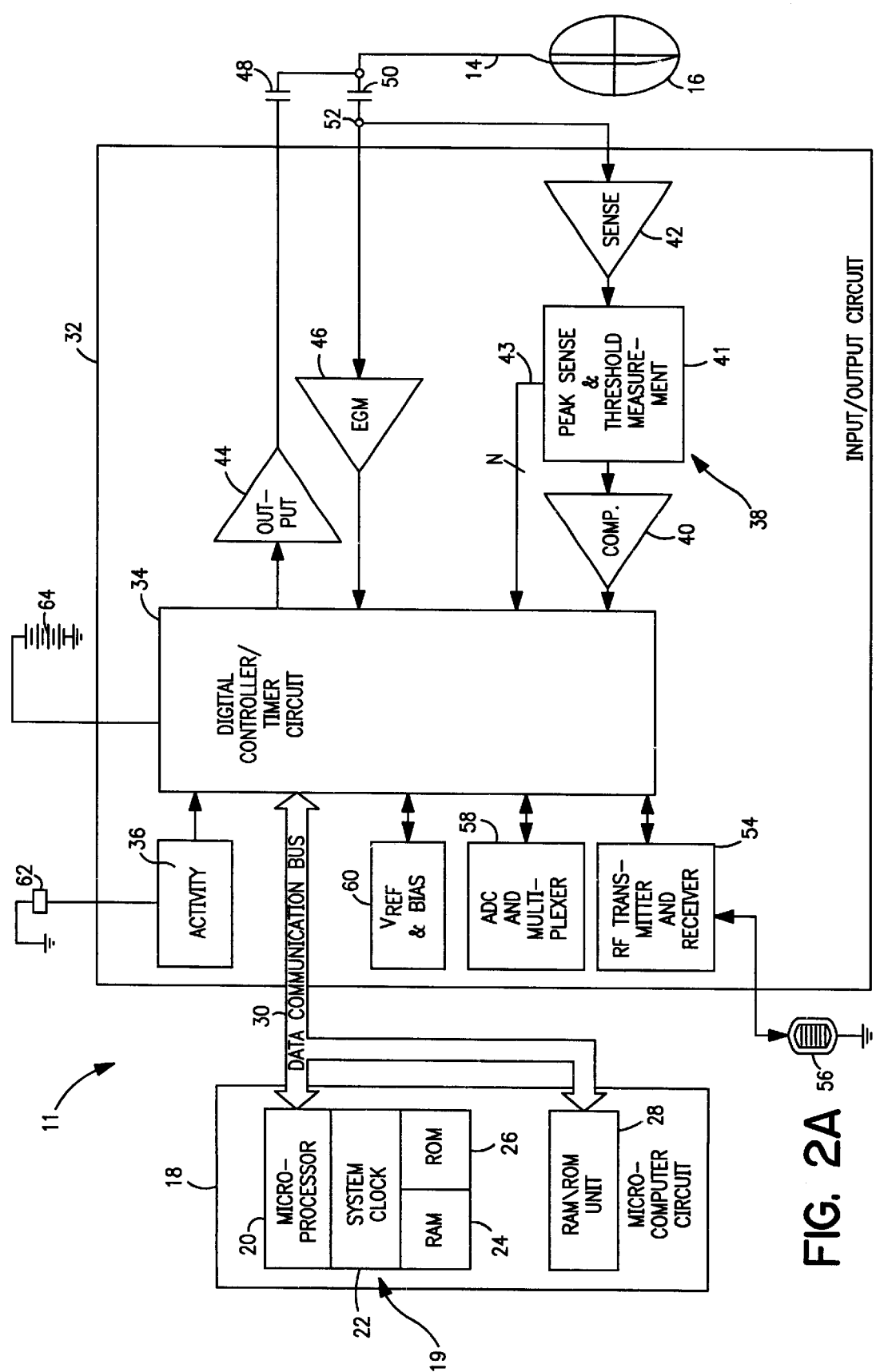
FIG. 2A shows one illustrative embodiment of a block diagram of an implantable pacemaker device including a processor according to the present invention.

FIG. 2A shows a block diagram illustrating components of a pacemaker 11 in accordance with one embodiment of the present invention where pacemaker 11 has a microprocessor-based architecture. However, the illustrative pacemaker device of FIG. 2A is only one exemplary embodiment using a microprocessor-based architecture which performs multiply and/or divide operations according to the present invention.

In the illustrative embodiment shown in FIG. 2A, the pacemaker 11 is preferably programmable by means of an external programming unit (not shown). One such programmer suitable for the purposes of the present invention is the commercially available Medtronic Model 9790 programmer. The programmer is a microprocessor device which provides a series of encoded signals to pacemaker 11 by means of a programming head which transmits radio frequency (RF) encoded signals to pacemaker 11 according to a telemetry system such as, for example, that described in U.S. Pat. No. 5,127,404 to Wyborny et al., the disclosure of which is hereby incorporated by reference herein in its entirety. It is to be understood, however, that any programming methodology may be employed so long as the desired information is transmitted to and from the pacemaker 11.

Pacemaker 11 illustratively shown in FIG. 2A is electrically coupled to the patient's heart 16 by lead 14. Lead 14 is coupled to a node 52 in the circuitry of pacemaker 11 through input capacitor 50. In the presently disclosed embodiment, an activity sensor 62 provides a sensor output to an activity circuit 36 of input/output circuit 32. Input/output circuit 32 also contains circuits for interfacing to heart 16, antenna 56, and contains circuits 44 for application of stimulating pulses to heart 16 to control its rate under control of software-implemented algorithms in microcomputer unit 18.

Microcomputer unit 18 preferably comprises on-board circuit 19 that includes microprocessor 20, system clock 22, and on-board random access memory (RAM) 24 and read only memory (ROM) 26. In this illustrative embodiment, off-board circuit 28 comprises a RAM/ROM unit. On-board circuit 19 and off-board circuit 28 are each coupled by a communication bus 30 to digital controller/timer circuit 34.

The electrical components shown in FIG. 2A are powered by an appropriate implantable battery power source 64 in accordance with common practice in the art. For the sake of clarity, the coupling of battery power to the various components of pacemaker 11 is not shown in the figures.

Antenna 56 is connected to input/output circuit 32 to permit uplink/downlink telemetry through RF transmitter and receiver unit 54. Unit 54 may correspond to the telemetry and program logic disclosed in U.S. Pat. No. 4,556,063 issued to Thompson et al., hereby incorporated by reference herein in its entirety, or to that disclosed in the above-referenced Wyborny et al. patent.

$V_{REF}$ and bias circuit 60 generates a stable voltage reference and bias currents for circuits of input/output circuit 32. Analog-to-digital converter (ADC) and multiplexer unit 58 digitizes analog signals and voltages to provide "realtime" telemetry intracardiac signals and battery end-of-life (EOL) replacement function.

Operating commands for controlling the timing of pacemaker 11 are coupled by bus 30 to digital controller/timer circuit 34, where digital timers and counters establish the overall escape interval of the pacemaker as well as various refractory, blanking, and other timing windows for controlling the operation of the peripheral components disposed within input/output circuit 32. Digital controller/timer circuit 34 is preferably coupled to sense circuitry 38, including sense amplifier 42, peak sense and threshold measurement unit 41, and comparator/threshold detector 40. Sense amplifier 42 amplifies sensed electrocardiac signals and provides an amplified signal to peak sense and threshold measurement circuitry 41. Circuitry 41 in turn provides an indication of peak sensed voltages and measured sense amplifier threshold voltages on path 43 to digital controller/timer circuit 34. An amplified sense amplifier signal is also provided to comparator/threshold detector 40. Sense amplifier 42 may correspond to that disclosed in U.S. Pat. No. 4,379,459 to Stein, which is hereby incorporated by reference herein in its entirety.

Circuit 34 is further preferably coupled to electrogram (EGM) amplifier 46 for receiving amplified and processed signals sensed by an electrode disposed on lead 14. The electrogram signal provided by EGM amplifier 46 is employed when the implanted device is being interrogated by an external programmer (not shown) to transmit by uplink telemetry a representation of an analog electrogram of the patient's electrical heart activity. Such functionality is, for example, shown in U.S. Pat. No. 4,556,063 to Thompson et al., hereby incorporated by reference herein in its entirety.

Output pulse generator 44 provides pacing stimuli to the patient's heart 16 through coupling capacitor 48 in response to a pacing trigger signal provided by digital controller/timer circuit 34. Output amplifier 44, for example, may correspond generally to the output amplifier disclosed in U.S. Pat. No. 4,476,868 to Thompson, also incorporated by reference herein in its entirety.

Figure 2B:
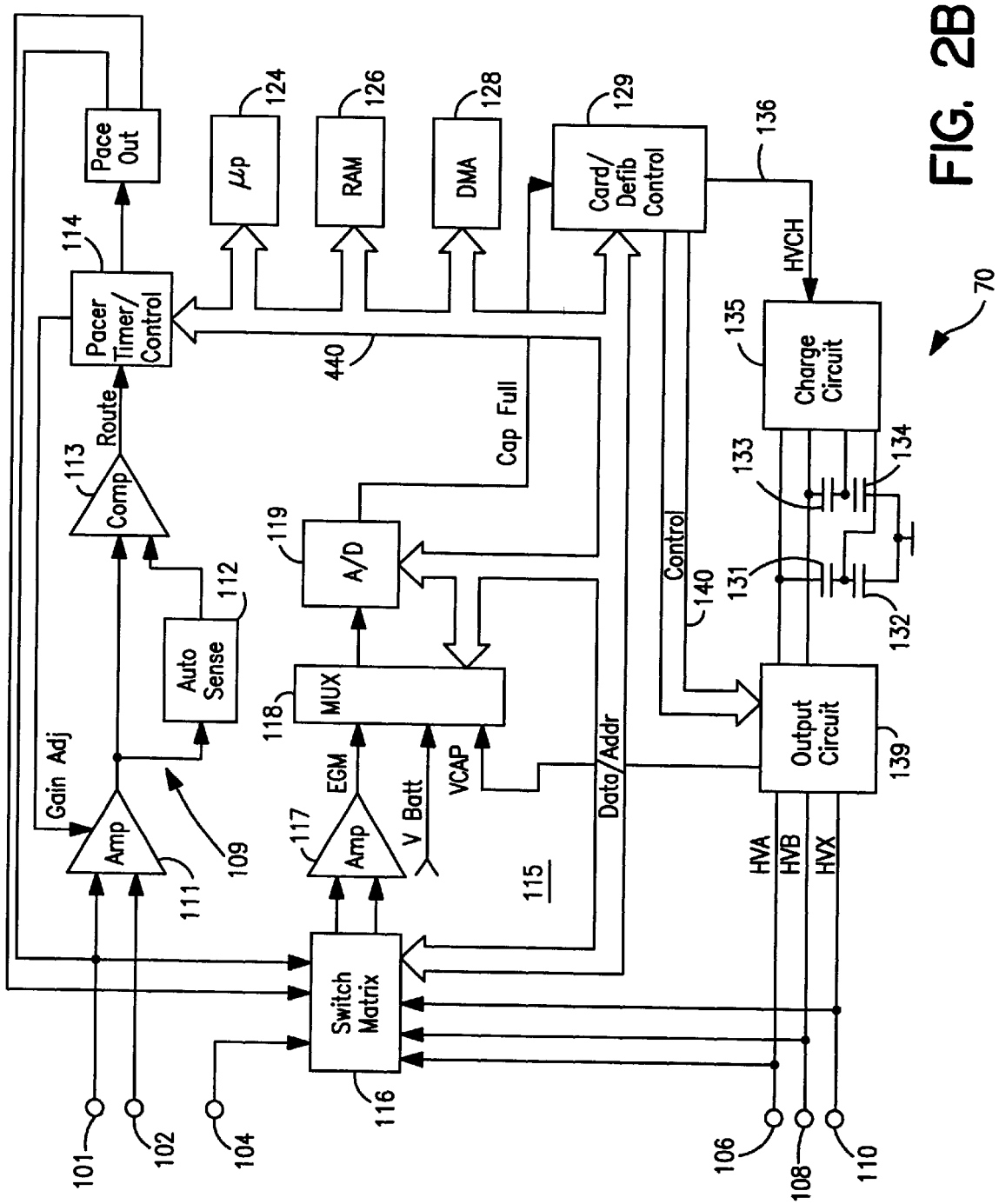
FIG. 2B shows one illustrative embodiment of a pacemaker/cardioverter/defibrillator including a processor according to the present invention.

FIG. 2B is a functional schematic diagram from U.S. Pat. No. 5,447,519 to Peterson which shows an implantable PCD 70 in which the present invention may be usefully practiced and which is incorporated by reference herein in its entirety. As indicated previously, this diagram is an illustration to be taken only as an exemplary type of device in which the invention may be embodied, and not as limiting to the scope of the present invention. Other implantable medical devices as previously described having functional organizations wherein the present invention may be useful may also be modified in accordance with the present invention. For example, the present invention is also believed to be useful in conjunction with implantable PCDs as disclosed in U.S. Pat. No. 4,548,209 to Wielders, et al.; U.S. Pat. No. 4,693, 253 to Adams et al.; U.S. Pat. No. 4,830,006 to Haluska et al.; and U.S. Pat. No. 4,949,730 to Pless et al.; all of which are incorporated herein by reference in their entireties.

The illustrative PCD device 70 is provided with six electrodes 101, 102, 104, 106, 108, and 110. For example, electrodes 101 and 102 may be a pair of closely-spaced electrodes located in the ventricle. Electrode 104 may correspond to a remote, indifferent electrode located on the housing of the implantable PCD 70. Electrodes 106, 108, and 110 may correspond to large surface area defibrillation electrodes located on device leads or to epicardial electrodes.

Electrodes 101 and 102 are connected to detector circuit 109 including band pass filtered amplifier 111, auto threshold circuit 112 (for providing an adjustable sensing threshold), and comparator 113. A signal is generated by the comparator 113 whenever the signal sensed between electrodes 101 and 102 exceed the sensing threshold defined by auto threshold circuit 112. Further, the gain of amplifier 111 is adjusted by pacer timing and control circuitry 114. The sense signal, for example, is used to set the timing windows and to align successive waveshape data for morphology detection purposes. For example, the sense event signal may be routed through the pacer/timer control circuit 114 on bus 115 to processor 124 and may act as an interrupt for the processor 124 such that a particular routine of operations is commenced by processor 124.

Switch matrix 116 is used to select available electrodes under control of processor 124 via data/address bus 115 such that the selection includes two electrodes employed as a far field electrode pair in conjunction with a tachycardia/ fibrillation discrimination function. Far field EGM signals from the selected electrodes are passed through band pass amplifier 117 and into multiplexer 118 where they are converted to multi-bit digital data signals by A/D converter 119 for storage in RAM 126 under control of direct memory access circuitry 128.

The processor 124 will perform various morphology detection functions. For example, such detection functions may be indicative of tachycardia or fibrillation, or various other functions may be performed as set out in numerous references including any of the references incorporated herein by reference and others with regard to implantable PCDs.

The remainder of the device 70 of FIG. 10 is dedicated to the provision of cardiac pacing, cardioversion, and defibrillation therapies. The pacer timing/control circuit 114 includes programmable digital counters which control the basic timing intervals associated with cardiac pacing. Further, under control of processor 124, pacer timing/control circuit 114 also determines the amplitude of such cardiac pacing pulses.

In the event that a tachyarrhythmia is detected, and an anti-tachyarrhythmia pacing therapy is desired, appropriate timing intervals for controlling generation of pacing therapies are loaded from processor 124 into pacer timing/control circuitry 114. Similarly, in the event that generation of a cardioversion or defibrillation pulse is required, processor 124 employs the timing/control circuitry 114 to control timing of such cardioversion and defibrillation pulses.

In response to detection of fibrillation or a tachycardia requiring a cardioversion pulse, processor 124 activates cardioversion/defibrillation control circuitry 129, which initiates charging of the high voltage capacitors 131–134 via charging circuit 135 under control of high voltage charging line 136. Thereafter, delivery of the timing of the defibrillation or cardioversion pulse is controlled by pacer timing/ control circuitry 114. One embodiment of an appropriate system for delivering and synchronization of cardioversion and defibrillation pulses, and controlling the timing functions related thereto, is disclosed in more detail in U.S. Pat. No. 5,188,105 to Keimel, which is incorporated herein by reference in its entirety. Other circuitry for controlling the timing and generation of cardioversion and defibrillation pulses is disclosed in U.S. Pat. No. 4,384,585 to Zipes, U.S. Pat. No. 4,949,719 to Pless et al., and in U.S. Pat. No. 4,374,817 to Engle et al., all incorporated herein by reference in their entireties. Further, known circuitry for controlling the timing and generation of anti-tachycardia pulses is described in U.S. Pat. No. 4,577,633 to Berkovitz et al., U.S.

Pat. No. 4,880,005 to Pless et al., U.S. Pat. No. 4,726,380 to Vollmann et al., and U.S. Pat. No. 4,587,970 to Holley et al., all of which are incorporated herein by reference in their entireties.

Selection of a particular electrode configuration for delivery of the cardioversion or defibrillation pulses is controlled via output circuit 139 under control of cardioversion/defibrillation control circuit 129 via control bus 140. Output circuit 139 determines which of the high voltage electrodes 106, 108 and 110 will be employed in delivering the defibrillation or cardioversion pulse regimen.

Figure 3:
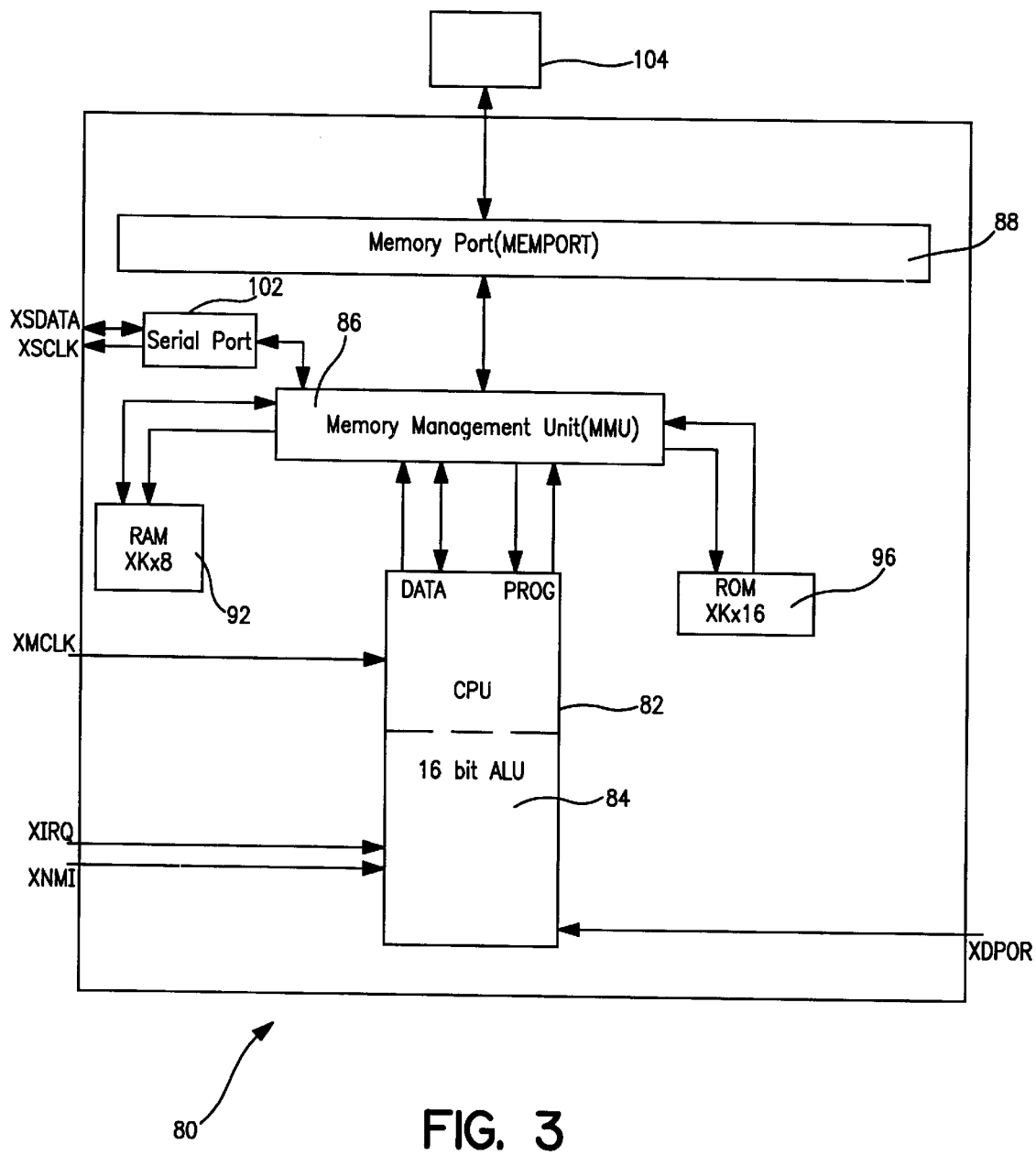
FIG. 3 shows a block diagram of a processor for performing multiply and/or divide operations according to the present invention.

According to the present invention, implantable medical device 12, such as that illustrated in the illustrative embodiments of the pacemaker 11 in FIG. 2A and the PCD device 70 of FIG. 2B, includes a data processor generally illustrated by the data processor 80 described herein with reference to FIG. 3. A portion of the central processing unit (CPU) 82 of the processor 80 is shown in further block detail in FIG. 4.

In general, the data processor 80 is exemplary of any low power microprocessor incorporating instructions according to the present invention as described herein for performing multiply and/or divide operations.

Particularly, the microprocessor is for medical devices where low power is required, e.g., implantable medical devices. A variety of low power processors such as the Motorola 6811C, the Intel 8052, can be used, configured, or modified for providing processing capabilities according to the present invention. It will be recognized by one skilled in the art that the instructions described herein or instructions of a similar nature may be beneficial for any processor design, e.g., 4-bit processors, 8-bit processors, 16-bit processors, 32-bit processors, 64-bit processors, etc.

The instructions described herein for performing multiply and/or divide operations simplify and increase the speed of execution of such operations. The instructions implement booth's algorithms efficiently in firmware. During multiply and/or divide processing, the microprocessor can have interrupts enabled, keeping interrupt servicing delay to acceptable values. Further, the instructions described herein enable low power, easy to use, interruptible integer multiply and divide operations. Such implementation of the multiply and divide operations provide exceptional benefits over other implementations which use either all hardware and/or all firmware to implement such operations.

In accordance with the present invention, four instructions act in concert to implement the multiply and/or divide operations. They include ADSCN, ADDCN, SRDX, ROLXD. Each instruction will be further described below.

As shown illustratively in FIG. 3, processor 80 includes central processing unit (CPU) 82; memory management unit (MMU) 86; ROM 96; RAM 92; memory port 88 for access to external ROM, RAM, and input/output devices, e.g., input/output circuit 32 (FIG. 2A); and serial port and controller 102 for access to a serial electrically programmable read-only memory (EEPROM) (not shown). It will be recognized that the amount of ROM and RAM may vary to provide different configurations. Further, other components of the system unrelated to the operation of the multiply and/or divide operations described below which communicate with the processor 80 may take various forms, e.g., timing and control circuits for pacemakers or PCDs, other CPU circuits, etc.

The CPU 82 forms the cornerstone of the processor 80 and carries out user-programmed algorithms. Preferably, the CPU 82 is connected to the other blocks in the system using a Harvard architecture. The Harvard architecture separates the program and data space using separate address and data busses for program and data memory. It will be readily apparent that other architectures which provide the functionality necessary for connection of the processor system may be used as would be recognized by one skilled in the art.

The desired sequence of CPU operations are stored in mass programmable instruction ROM 96. Preferably, there are sufficient words of ROM on-chip, with a word length of 16-bits. Most CPU instructions require one 16-bit word of ROM. The ROM may be accessed as data during selected CPU instructions providing ROM table look-up capability.

The CPU RAM 92 may be used for temporary data storage and also to implement software algorithms such as event calendars, etc. Preferably, there are sufficient bytes of RAM on-chip. The RAM data may be accessed in 8-bit bytes or 16-bit words. Portions of the RAM may be accessed as instruction data providing for downloadable programs.

The MMU 86 works in conjunction with the CPU to generate the correct address and steer data during program and data access. The MMU 86 is considered a single block for simplicity purposes but is actually part of many blocks within the processor 80. For example, the MMU is used to manage the 8-bit and 16-bit traffic in and out of the CPU 82.

General purpose memory port 88 is provided for communication to and from the processor 80 with off-chip peripheral devices generally shown as block 104. Memory port 88 is under software control and utilizes an address bus and a data bus to allow processor 80 to preferably address data memory and program memory.

Serial port 102 is preferably a two-wire serial port and controller for providing communication to a serial programmable device. For example, in a pacing system such as described with reference to FIG. 2A, serial port controller is managed by firmware writes and reads to memory mapped registers located on the processor 80. A serial programmable memory (not shown) would contain model numbers, key pacing parameters, and instruction code.

The processor 80 is preferably configured to work with 8-bit or 8/16-bit (i.e., 8-bit and 16-bit) data external memories as would be recognized by one skilled in the art. However, as previously mentioned, the present invention is applicable to other processors, e.g., 4-bit and 32-bit processors as well as 8-bit and 16-bit processors. Such external memory configurations are shown generally by reference numeral 104. It will be readily apparent that various interconnect configurations can be used so that the processor 80 is useable with off-the-shelf memories.

Various inputs and outputs are labeled for the processor 80 as shown in FIG. 3. One skilled in the art will readily recognize that such inputs and outputs may vary in accordance with the particular processor specifications. For illustrative purposes, various inputs and outputs shall be generally described.

The serial port 102 which interfaces with programmable read-only memory includes a serial data pin-XSDATA. This is a bidirectional pin used to transfer addresses and data into and out of the serial programmable read-only memory device (not shown). XSCLK is used to provide a clock to synchronize the data transfer between the processor 80 and the serial programmable read-only memory.

The inputs XIRQ and XNMI are used by external ICs (not shown) (e.g., pacemaker and PCD controller ICs) to interrupt the CPU 82. The XIRQ input is used to generate a maskable CPU interrupt. This maskable CPU interrupt will suspend CPU 82 normal program operation and ISR operation if the I-bit in the processor status word is set. The XNMI interrupt is non-maskable in that this interrupt will suspend CPU normal program operation and ISR operation regardless of the status of the I-bit in the processor status word. Upon receiving one of these interrupts, the CPU 82 will complete its current instruction, suspend program operation, save the program counter, processor status word, and the direct page register (DPR) on the stack, and jump to one of the interrupt service routine (ISR) locations. Processor interrupt is described further below.

The XMCLK-master clock input provides the master clock for CPU 82 operation. This clock is supplied by an external IC (not shown).

Lastly, with respect to the inputs and outputs of processor 80, XDPOR is used to reset the processor 80 to power on reset (POR) conditions which are of known state. Further, the processor 80 is provided with power ground and reference connections.

The interrupt process for processor 80 shall be described in further detail according to the present invention. The implementation for performing multiply and/or divide operations provide interruptible multiply and divide capability. The instructions executed in response to an interrupt are called the interrupted service routine (ISR). Such routines are much like subroutines except that they are called through an automatic hardware mechanism rather than through software control. In addition, before ISRs are called, selected registers are saved on the stack; whereas during a subroutine call, only the program counter is saved.

Figure 5:
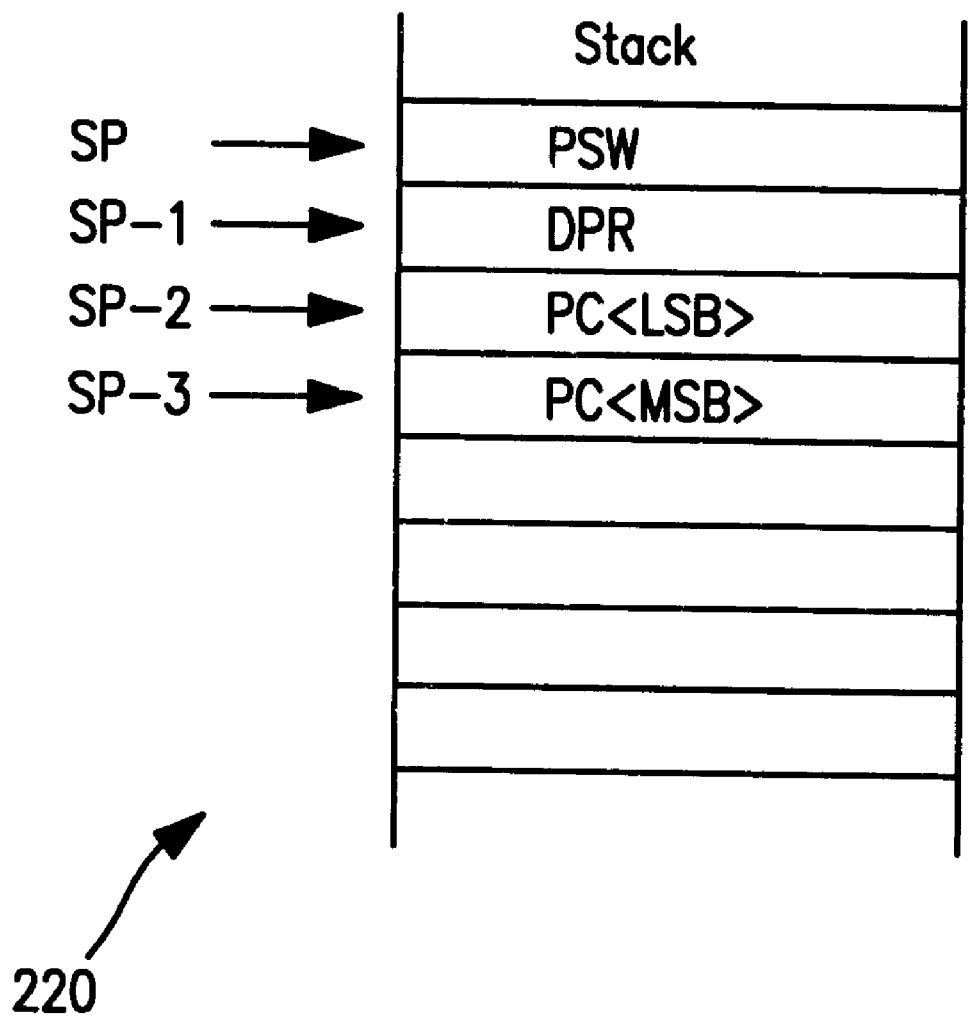
FIG. 5 shows a diagram of a stack including data stored upon an interrupt according to the present invention.

An interrupt, i.e., any signal leading to the performance of an ISR, causes normal program execution to be suspended as soon as the currently executing instruction is completed. The interrupt logic then pushes the processor status word (PSW), the direct page register (DPR), and contents of the program counter (PC) onto the stack so that these registers can be restored after the interrupt operation is complete. FIG. 5 shows the stacking order upon interrupt. The general purpose registers (A, B, X, Y) and the bank select register (BSR) are not automatically saved on the stack. However, the beginning of an ISR may contain an instruction or any combination of instructions to save certain other registers on the stack. For example, when a multiply or divide operation is performed the A, B, X, Y registers may be saved upon an operation of an ISR.

After stacking the selected CPU registers, the CPU 82 executes the instruction corresponding to the interrupt source. Inside each ISR, instructions are executed which determine the interrupting source (if necessary) and the proper interrupt operation is performed.

An interrupt operation is concluded when a return from interrupt instruction (RTI) is executed. This causes the selected CPU registers and the return address (PC) to be recovered from the stack allowing the interrupted program to resume as if there had been no interruption. All instructions are interruptible. Any instruction which is interrupted will complete before performance of the appropriate ISR.

The processor 80 may have any number of interrupt sources. As previously described, the XIRQ and XNMI interrupts are generated external to the processor 80. Other interrupts are generated internal to the processor 80. The XIRQ is a primary interrupt for processor 80 operation. For example, the XIRQ interrupt is maskable and typically may be generated by multiple sources in the system using the processor 80. For example, in pacing systems, timers, pacing events, etc. may generate such interrupts. The XIRQ interrupt is level sensitive and can be activated by one or more integrated circuits (ICs) in the pacing system. Various other interrupts are possible. For example, if an instruction is suspect, an interrupt may be generated to perform an ISR.

It will be recognized that in the case of two or more interrupts occurring at the same time, the interrupts can be prioritized so that one unique interrupt is identified. For example, such interrupts may be prioritized with the more important interrupts, e.g., XIRQ, having a higher priority than the others.

Controller ICs, e.g., timing/controller ICs 34 of the pacing system 11 or timing control ICs 114 of PCD 70, typically generate interrupts for the processor 80. For example, the XIRQ interrupt may be generated by one or more ICs in the pacing system. The interrupt may be generated by multiple sources from these ICs. Further, an interrupt register (or registers) may be located on one or more of these external ICs. This interrupt register will be customized for the logic and functionality of the external ICs.

Preferably, the data processor 80 is a 16-bit processor with a 16-bit ALU 84 and includes 8-bit and 16-bit registers. Preferably, the ALU 84 is 16-bits so that the multiply and divide tasks can be performed quickly.

Figure 4:
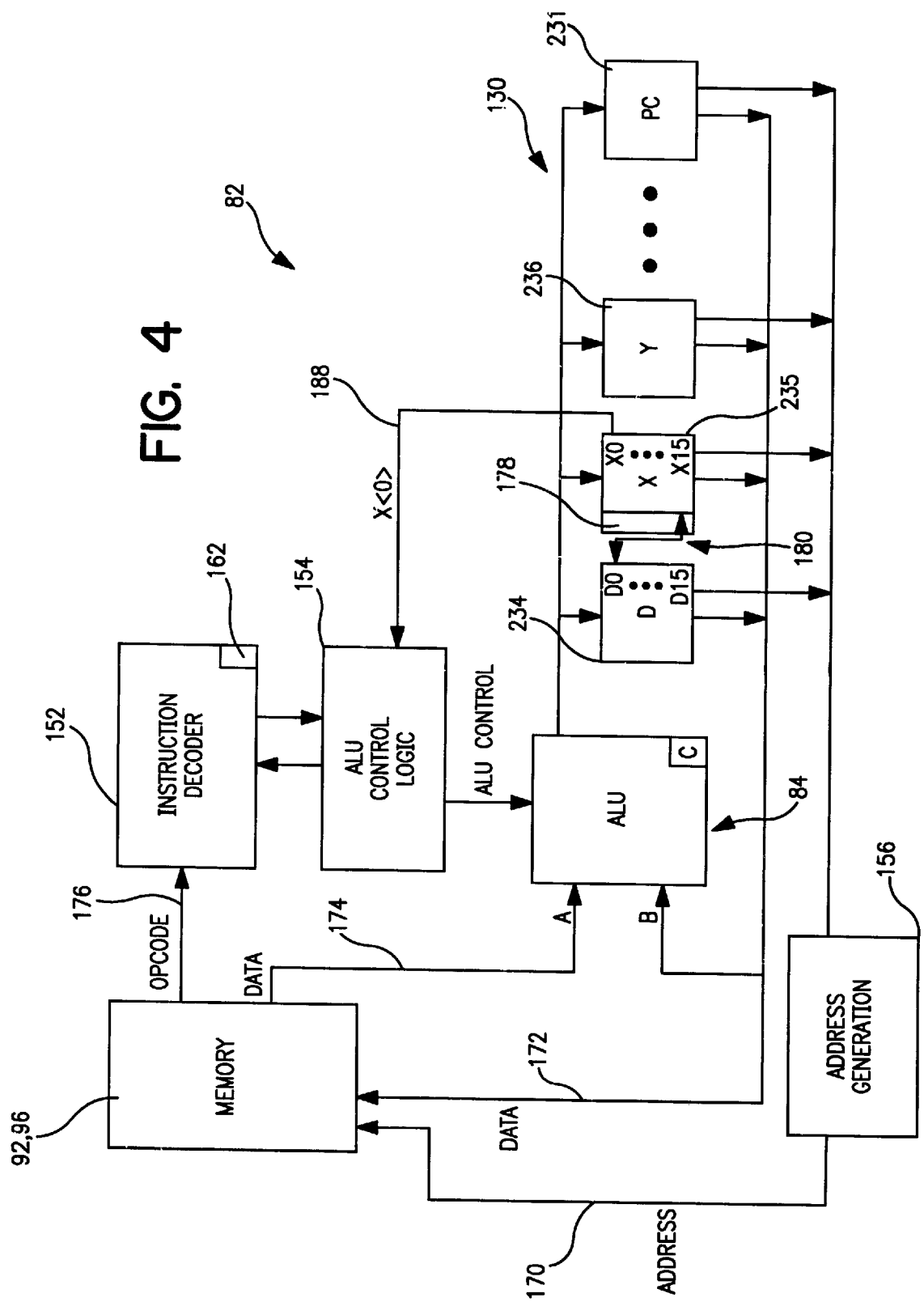
FIG. 4 shows a block diagram of at least a part of the CPU of the processor of FIG. 3 according to the present invention.
Figure 6:
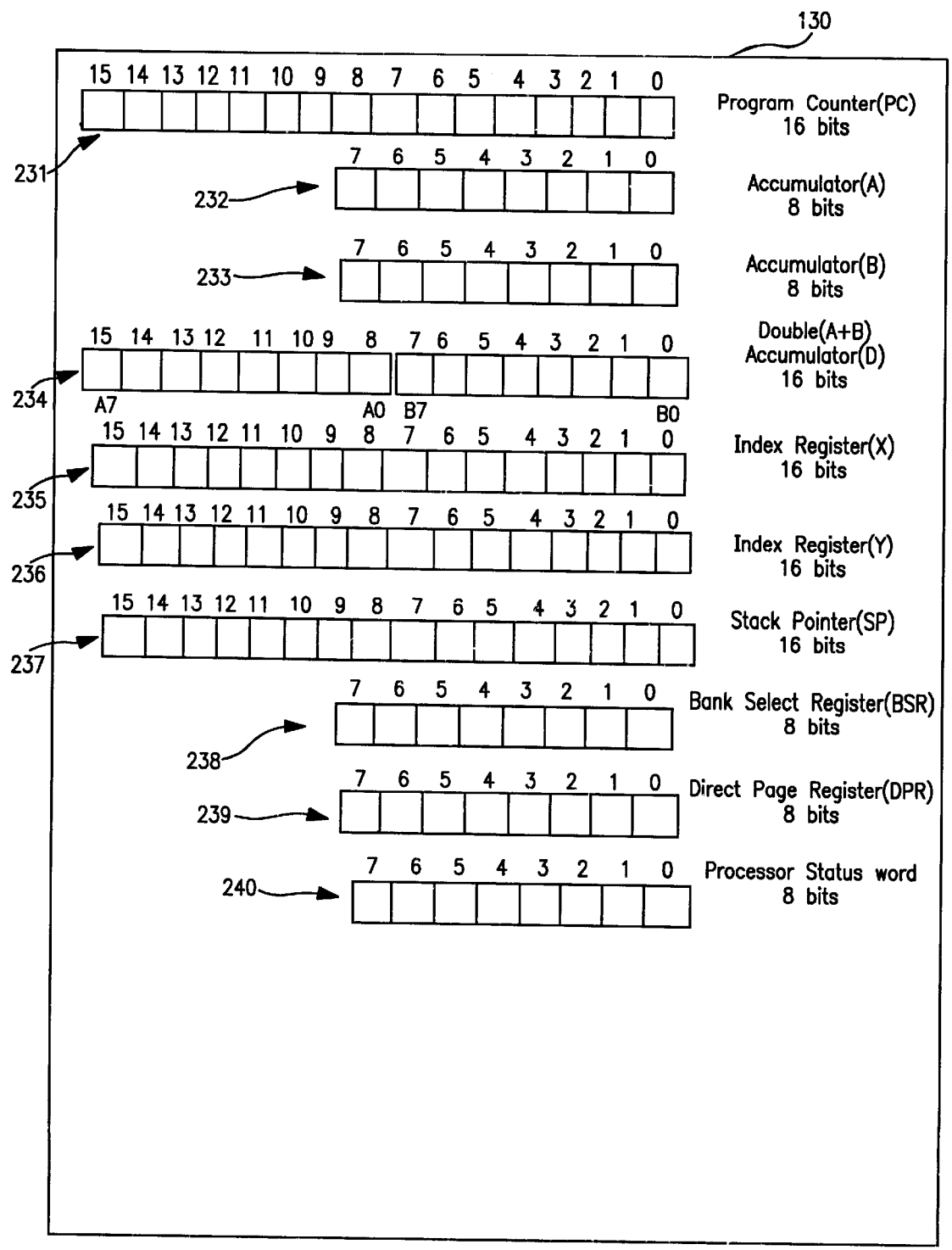
FIG. 6 shows a diagram of a set of registers for the processor of FIG. 3.

As shown generally in FIG. 4, processor 80 includes memory, RAM 92 and ROM 96. Further, generally, the CPU 82 includes an instruction decoder 152, control logic 154, address generation block 156, the ALU 84, and register set 130. A summary of various registers of the processor register set 130 is shown in FIG. 6. Preferably, the processor register set 130 includes: 8-bit accumulators (A) and (B) 232, 233; 16-bit accumulator (D) 234 (combines A and B for 16-bit capability); 16-bit index registers (X) and (Y) 235, 236; 8-bit direct page register (DPR) 239; 8-bit bank select register (BSR) 238; 16-bit stack pointer (SP) 237; 16-bit program counter (PC) 231; and 8-bit processor status word (PSW) 240. A, B—accumulators 232, 233 are general purpose 8-bit accumulators. They are preferably used to hold operands and results of ALU 84 data operations. These are the main registers used in arithmetic and logic manipulation. D—double accumulator 234 is preferably used when instructions treat the combination of the A and B-accumulators 232, 233 as a 16-bit double accumulator.

X, Y—index registers 236, 237 are 16-bit index registers that preferably are used for an indexed addressing mode of operation. In the indexed addressing mode, the contents of the 16-bit index register are added to an 8-bit offset to form the effective address of an operand. Two forms of indexed addressing are available: no offset and 8-bit offset. The no offset mode is achieved by specifying a zero offset.

DPR—direct page register 239 is an 8-bit register that preferably contains the most significant byte of the address to be used in a direct addressing mode of operation. In this mode, the contents of this register are concatenated with 8-bits in the opcode to form a 16-bit address.

BSR—bank select register 238 is an 8-bit register that preferably contains the upper 8-bits of a RAM address for all data (RAM) addressing modes. These 8-bits are concatenated with the lower 16-bits to form a 24-bit RAM address.

SP—stack pointer 237 is a 16-bit register preferably used to address the CPU stack (FIG. 5). PC—program counter 231 is the 16-bit register which preferably holds the address of the next instruction to be executed.

PSW—processor status word register 240 is a register that preferably contains four status flags which reflect the results of executing most instructions and four enable bits which control normal and test functions. The status flags are the zero flag (Z), negative flag (N), carry/borrow flag (C), and overflow flag (V). The four enable bits are the interrupt enable bit (I), the DPR enable bit (D), the BSR enable bit (B), and single step enable bit (S). All bits in the PSW 240 are saved on the stack during interrupts.

The four status flags are further described. Z—the zero flag indicates whether or not the result of the last operation was zero. N—the negative flag indicates whether or not the result of the last operation was negative (i.e., the state of the most significant bit (MSB) of the result). For the twos complement number representation, a number is negative when the MSB is set, and is positive when the MSB is zero. C—the carry flag indicates whether or not a carry/borrow occurred in the last operation. The C flag is set based on the carry or borrow from bit 7 during 8-bit operations and from bit 15 during 16-bit operations. V—the overflow flag indicates that a twos complement overflow has occurred as a result of the last operation. An overflow occurs during addition or subtraction when a carry/borrow is generated into but not out of the sign bit or is generated out of but not into the sign bit. The sign bit refers to the sign bit of the result. For example, the sign bit is bit 7 during 8-bit operations and bit 15 during 16-bit operations.

The I bit is the master interrupt enable bit which controls maskable interrupt operation. For example, when this bit is set (e.g., one), the maskable interrupt, XIRQ, will be allowed to interrupt the CPU. When it is not set (e.g., zero), the interrupt is ignored. An interrupt which is pending is serviced as soon as the I-bit is set back to a logic one. The D bit is used to enable the direct page register (DPR). The B bit is used to enable the bank select register (BSR). When this bit is set (e.g., one), the BSR is used to extend the data addressing capability of the processor 80 to a larger amount of memory.

Preferably, the primary registers used to carry out the multiply and divide operations according to the present invention as shown in the illustrative embodiment below include the D-accumulator 234, the X-index register 235, the Y-index register 236, the PC-program counter 231, and the processor status word (PSW). However, the present invention may be carried out using various other registers as will be recognized by one skilled in the art from the description herein. For example, the accumulator may be implemented using any register that serves to provide an accumulation function and the function of the X-index register as a part of the connected shift path may be fulfilled by any other like register. Further, such registers may be registers added to the processor in addition to the already available set of registers generally available for the processor. However, use of already available registers is preferred to eliminate the need for additional structure and design for the processor. The operation of such registers for carrying out the multiply and divide functions shall be described in detail below.

In processor 80, the instruction word contains two kinds of information: the type of operation to be performed (termed the "opcode") and the location of the operand(s) on which to perform that operation. The addressing mechanism is used to specify the location of these operands. Processor 80 preferably supports various commonly used addressing modes. For example, such addressing modes include those of various ICs including those of the 6811C available from Motorola and GME, and of the 8052 available from Intel. Numerous addressing modes may be used in the CPU 82. A description of several addressing modes applicable to multiply and divide operations along with the word formats associated therewith are described in the following paragraphs. For the word formats, OCn, Dn, On, and An denote bit n of the opcode, data, address offset, and address for the argument, respectively. However, the present invention is not limited to such addressing modes.

Figure 7A:
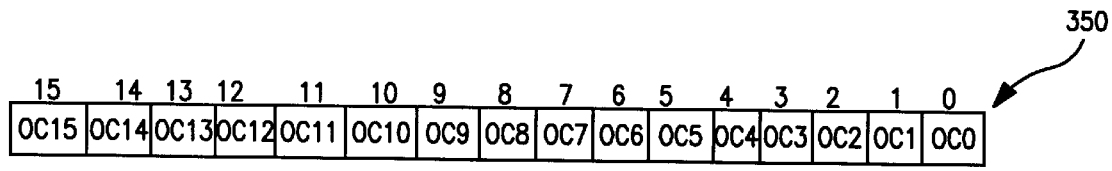
FIGS. 7A, 7B, 7C and 7D show diagrams of various bit formats for certain instructions according to the present invention.

In implied or inherent addressing, the instruction implies the use of specific registers and/or other operands. No operand location information is supplied in the instruction mnemonic because everything that is needed to execute the instruction is inherently known by the CPU 82. The operands, if any, are registers and thus are not fetched from memory. Such is the case for the SRDX instruction and ROLXD instruction used for the multiply and divide operations. The word format 350 for this mode is shown in FIG. 7A.

Figure 7B:
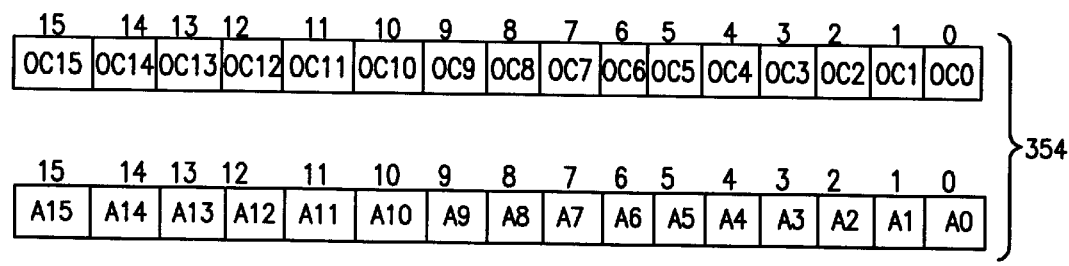

In the extended addressing mode (EXT), the 16-bit effective address (A0–A15) is contained in the word following the opcode. When BSR register is enabled, the 8-bits of the BSR are concatenated with these 16-bits to form a 24-bit address which addresses data. The word format 354 for extended addressing is shown in FIG. 7B.

Figure 7C:
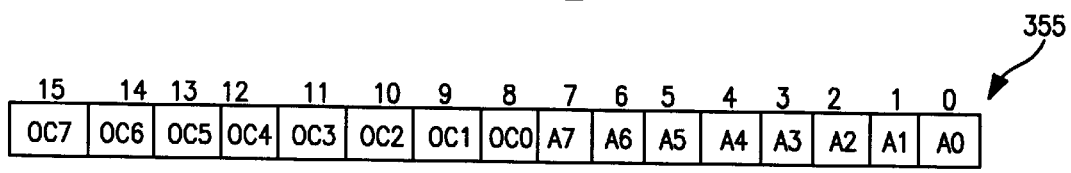

In the direct addressing mode (DIR), the lower 8-bits of the effective address (A0–A7) are contained in the instruction word along with the opcode. The upper 8-bits of the 16-bit effective address are contained in the DPR-direct page register 239. When the BSR is enabled, the 8-bits of the BSR are concatenated with these 16-bits to form a 24-bit address which addresses data. The word format 355 for direct addressing is shown in FIG. 7C.

In indexed addressing mode (INDX, INDY), either index register X or Y is used in calculating the effective address. Two modes of indexing are available: No offset and 8-bit offset. In the no offset mode, the offset (O0–O7) is set to zero. In this case, the index register X or Y contains the 16-bit effective address. When the offset is other than zero, the contents of index register X or Y are added to the 8-bit unsigned offset contained in the opcode.

When the BSR is enabled, the 8-bits of the bank select register are concatenated with the resulting 16-bits (index register+offset) to form a 24-bit address which addresses data. When the BSR is disabled, the upper 8-bits of the 24-bit effective address are set to zero.

Figure 7D:
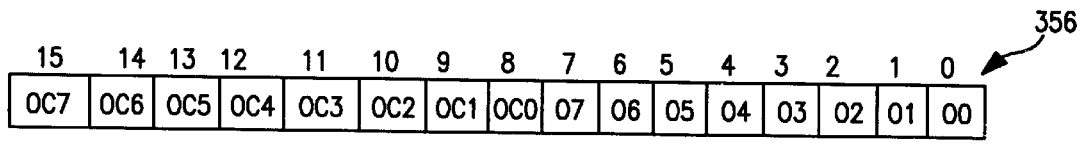

Indexed addressing is utilized by mnemonic instructions ending in "X" or "Y." The word format 355 for indexed addressing is shown in FIG. 7D.

In the context of the above description, four novel instructions act in concert to implement the multiply and/or divide operations (i.e., subroutines) for processor 80 as will be described particularly with reference to FIG. 4. The multiply and divide subroutines are performed using a conditional add/subtract instruction (ADSCN); a conditional add instruction (ADDCN); a shift right D and X registers instruction (SRDX); and a rotate left X and D registers instruction (ROLXD). In practice, a multiply or a divide subroutine is called to be performed during performance of a function by the processor 80. The routine is accessed and stored in memory 92, 96. The PC-program counter 231 steps the processor 80 through the instructions of such routines to perform such operations.

Generally, an illustrative multiply subroutine for carrying out a 16-bit multiplication (16×16=32 bits) is shown below where the 32-bit result is the D-accumulator:X-index register.

Multiply:

| | |
|---|---|
| clrd | (i.e, clear D-accumulator instruction) |
| addcn 0,y | |
| srdx | |
| addcn 0,y | |
| srdx | |
| addcn 0,y | |
| srdx | |
| addcn 0,y | |
| srdx | |
| addcn 0,y | |
| srdx | |
| addcn 0,y | |
| srdx | |
| addcn 0,y | |
| srdx | |
| addcn 0,y | |
| srdx | |
| addcn 0,y | |
| srdx | |
| addcn 0,y | |
| srdx | |
| addcn 0,y | |
| srdx | |
| addcn 0,y | |
| srdx | |
| addcn 0,y | |
| srdx | |
| addcn 0,y | |
| srdx | |
| addcn 0,y | |
| srdx | |
| addcn 0,y | |
| srdx | |
| rts | (i.e., return to program instruction) |

Generally, an illustrative divide subroutine for carrying out a 16-bit division (16×16=16) is shown below where the 16-bit quotient of the result is the X-index register with the remainder in the D-accumulator.

Divide:

| | |
|---|---|
| clrd | (i.e, clear D-accumulator instruction) |
| rolxd | |
| adscn 0,y | |
| rolxd | |
| adscn 0,y | |
| rolxd | |
| adscn 0,y | |
| rolxd | |
| adscn 0,y | |
| rolxd | |
| adscn 0,y | |
| rolxd | |
| adscn 0,y | |
| rolxd | |
| adscn 0,y | |
| rolxd | |
| adscn 0,y | |
| rolxd | |
| adscn 0,y | |
| rolxd | |
| adscn 0,y | |
| rolxd | |
| adscn 0,y | |
| rolxd | |
| adscn 0,y | |
| rolxd | |
| adscn 0,y | |
| rolxd | |
| adscn 0,y | |
| rolxd | |
| adscn 0,y | |
| rolxd | |

-continued

| | |
|---|---|
| adscn 0,y | |
| rolxd | (i.e., normal rotate left of just the X-register) |
| addcn 0,y | (i.e., to format remainder) |
| comx | (i.e., complement quotient instruction given by $\overline{X} \rightarrow X$, where X is the quotient of the result) |
| rts | (i.e., return to program instruction) |

In general, the instructions used in the multiply and divide subroutines are performed according to the following description with reference to FIG. 4. Memory 92, 96 is used to store the subroutine called and provide instruction words including at least operations code (opcode) on opcode line 176 to the instruction decoder 152 as appropriate to provide the instructions required to be performed. Instruction decoder 152 includes decode circuitry for decoding instructions of the instruction set available for processor 80, including multiply and divide instruction decode circuitry 162 for decoding the instructions ADDCN, ADSCN, ROLXD, and SRDX. The instruction word will take the form of one of the previously described formats for the various addressing modes.

Upon decoding of the ADDCN instruction, if conditional bit X<0> of X-index register 235=1 as indicated by line 188, then the ALU control logic 154 is set to an add function to control ALU 84. Further, the contents of the D-accumulator 234 D<15:0> is provided to the B input of the ALU 84 and data of the specified effective address is present to input A of the ALU 84 per data line 174. The data of the specified effective memory address is the memory operand addressed the addressing modes used. The ALU 84 then adds the two numbers applied to the A and B inputs and stores back the results into the D-accumulator 234. Thereafter, the program counter 231 is incremented to control the provision of the next instruction word of the multiply or divide routine from memory to the instruction decoder 152 by way of address generation block 156.

On the other hand, also upon decoding of the ADDCN instruction, if the conditional bit X<0>=0 as indicated by line 188, then either a zero is added to the contents of D-accumulator 234 and the result is saved back to the D-accumulator 234 or nothing is performed prior to incrementing of the program counter 231 to address the next executable instruction/word through address generation block 156. The instruction word addressed is applied from memory 92, 96 to instruction decoder 152.

Upon decoding of the ADSCN instruction, if the conditional bit X<0>=1 as indicated by line 188, then the ALU control logic 154 is set to an add function for control of ALU 84. Further, the contents of the D-accumulator D<15:0> is provided to the B input of the ALU 84 per data line 172 and data of the specified effective address is presented to input A of the ALU 84 per data line 174. The ALU 84 then adds the two numbers applied to the A and B inputs and stores back the results into the D-accumulator 234. Thereafter, the program counter 231 is incremented to control the provision of the next instruction/word of the multiply or divide routine from memory to the instruction decoder 152.

On the other hand, also upon decoding of the ADSCN instruction, if the conditional bit X<0>=0, then the ALU control logic 154 is set to a subtract function for control of ALU 84. Further, the content of the D-accumulator D<15:0> is provided to the B input of the ALU 84 and data of the specified effective address is present to input A of the ALU 84. The ALU 84 then subtracts the two numbers applied to the A and B inputs and stores back the results into the D-accumulator 234. Thereafter, the program counter 231 is incremented to control the provision of the next instruction/word of the multiply or divide routine from memory to the instruction decoder 152.

The conditional bit as described herein may be one or more bits indicative of a set state and a state that is not set. Preferably, the conditional bit is a single bit representative of a set or unset state. The set state, for example, may be a "one" bit representative of a set state and a "zero" bit may represent the condition when the state is not set. However, such set and unset states, may, for example, be reversed.

Further, the conditional bit may be part of any number of different registers or a state provided or initiated through other circuitry. For example, the conditional bit may be the most significant bit (MSB) of an index register, e.g., X index register, which may allow for shifting of the bits of the shift path in the reverse direction from that described in detail below. Preferably, the conditional bit is the least significant bit (LSB) of the x-register or any other register used as the shift path register in combination with the accumulator to form the shift path according to the present invention as described further below.

Upon decoding of an ROLXD instruction, the carry bit "C" 164 which is the carry flag bit stored in the ALU 84, the bits of the D-accumulator 234, and the bits of the X-index register 235 are all connected (i.e., combined) together into one long 33-bit chain, i.e, shift path 180. The bits of the chain are each rotated to the left one bit position. The shift path 180 between the D<0> bit and the X<15> bit connects the two 16-bit registers together. Shift logic 178 attached to the X-index register 235 is used to rotate the bits of the X-index register 235 one position to the left. The bits of the D-accumulator 234 are shifted using the ALU 84. The D<15> bit is shifted to carry bit C 164 and the carry bit C is shifted to X<0>.

Upon decoding of an SRDX instruction, the carry bit "C" 164 which is the carry flag bit stored in the ALU 84, the bits of the D-accumulator 234, and the bits of the X-index register 235 are all connected together into one long 33-bit chain, i.e., shift path 180. The bits of the chain are then each shifted to the right one bit position. The shift path 180 between the D<0> bit and the X<15> bit connects the two 16-bit registers together. Shift logic 178 attached to the X-index register 235 is used to shift the bits of the X-index register 235 one bit position to the right. The bits of the D-accumulator 234 are shifted using the ALU 84. The carry bit C 164 is shifted into D<15> and the bit of X<0> is not saved. However, in alternative embodiments, carry bit may not be discarded. The connection of the registers to form the 33-bit chain and to accomplish such rotation or shifting of the bits of the chain can be performed in any manner.

The shift path 180 is preferably formed using an accumulator, another register (e.g., X-index register), and carry bit C 164. However, the carry bit C 164 may not be required in the shift path 180. Further, the instructions defined above may be carried out using any type of registers of the register set and further any additional registers which allow the functions of the instructions to be accomplished. For example, the accumulator may be implemented using any register that serves to provide an accumulation function. Further, in addition to the accumulator or like register, the shift path may be formed using other registers like the X-index register, e.g., Y-index register, or any other register usable to accomplish the functionality of a shift path register which combined with the accumulator form a suitable shift path for use according to the present invention. Further, as previously described, such functionality may be provided by registers added to the processor in addition to the already available set of registers generally used for executing other instructions for the processor. However, use of already available registers is preferred to eliminate the need for additional structure and design for the processor. As such, one skilled in the art will recognize that the multiply/divide operations as described herein are not limited to use with the specific illustrative registers, accumulators, etc. as described herein with reference to specific configurations.

In more detail, the multiply and divide instructions are provided below.

ADSCN—Conditional Add/Subtract Instruction

The operation of ADSCN is:

If X0=1, D+(M:M+1)->D,

Else, D-(M:M+1)->D

In other words, if Bit 0 of the X-index register is set, add the current contents of the D-accumulator to the operand and save back to the D-accumulator. If Bit 0 of the X-index register is clear, subtract the operand from the current contents of the D-accumulator and save back to the D-accumulator. The operand is the data at the specified effective address concatenated with the data located at that address+1. ADSCN is a 16-bit operation.

Table 2 shows the conditional add operation (i.e., Bit 0 is set) in more detail using various addressing modes.

TABLE 2

Conditional Add (ADSCN)

| Address Mode | Syntax | Cycle 1 | Cycle 2 |
|---|---|---|---|
| DIR | ADSCN $aa | D+[$bbppaa]:[$bbppaa+1]->D | — |
| EXT | ADSCN $aaaa | pc+1->pc | D+[$bbaaaa]:[$bbaaaa+1]->D |
| INDX(Y) | ADSCN $dd,Y | Y+$dd->Temp a | D+[$bbaaaa]:[$bbaaaa+1]->D |
| INDX(Y)$_{0-}$ offset | ADSCN O,Y | D+[$bbyyyy]:[$bbyyyy+1]->D | — |

Table 3 shows the conditional subtract operation (i.e., Bit 0 is clear) in more detail using various addressing modes.

TABLE 3

Conditional Subtract (ADSCN)

| Address Mode | Syntax | Cycle 1 | Cycle 2 |
|---|---|---|---|
| DIR | ADSCN $aa | D-[$bbppaa]:[$bbppaa+1]->D | — |
| EXT | ADSCN $aaaa | pc+1->pc | D-[$bbaaaa]:[$bbaaaa+1]->D |
| INDX(Y) | ADSCN $dd,Y | Y+$dd->Temp a | D-[$bbaaaa]:[$bbaaaa+1]->D |
| INDX(Y)$_{0-}$ offset | ADSCN O,Y | D-[$bbyyyy]:[$bbyyyy+1]->D | — |

The flags which are affected in the ADSCN instruction in certain cases include:

N—Set if MSB of result is set to one; else clear. (R15)

Z—Set if result is $0000; else clear.

V—Set for two's complement overflow; else clear.

C—Set based on the exclusive or of the carry flag prior to the instruction (Cin) and the carry from the MSB of result (Cout) (i.e., C=(Cin±Cout)).

ADDCN-Conditional Add Instruction

The operation of ADDCN is:

If X[0]=1,

D+(M:M+1)->D

In other words, if Bit 0 of the X-Index Register is set, add the current contents of the D-accumulator to the operand and the save back to the D-accumulator. If Bit 0 is clear, PC is incremented to the next executable instruction. The operand is the data at the specified effective address concatenated with the data located at that address+1. AD DCN is a 16-bit operation.

Table 4 below shows oper ation assuming x[0] is set.

TABLE 4

Conditional Add (ADDCN)

| Address Mode | Syntax | Cycle 1 | Cycle 2 |
|---|---|---|---|
| DIR | ADDCN $aa | D+[$bbppaa]:[$bbppaa+1]->D | — |
| EXT | ADDCN $aaaa | Pc+1->pc | D+[$bbaaaa]:[$bbaaaa+1]->D |
| INDX(Y) | ADDCN $dd,Y | Y+$dd->Temp a | D+[$bbaaaa]:[$bbaaaa+1]->D |
| INDX(Y)$_{0-}$ offset | ADDCN O,Y | D+[$bbyyyy]:[$bbyyyy+1]->D | — |

The flags which are affected in certain cases include:

N—Set if MSB of result is set to one; else clear. (R15)

Z—Set if result is $0000; else clear.

V—Set for two's complement overflow; else clear.

C—Set if carry from the MSB of result; else clear.

SRDX—Shift Right D & X Registers Instruction

The operation of SRDX is:

C->D15:0->X15:0

In other words, SRDX effectively performs a 33-bit shift right. All bits of the carry flag, the 16-bit D-accumulator and the 16-bit X-index register are treated as one 33-bit word. The carry flag is placed into the MSB of D-accumulator, and all other bits are shifted right one position. The pre-shift value of the LSB of the X-index register is not saved. SRDX is an inherent operation. The operation is shown in Table 5.

TABLE 5

SRDX

| Address Mode | Syntax | Cycle 1 |
|---|---|---|
| Inherent | SRDX | C -> D15:0 -> X15:0 |

No flags are affected.

ROLXD—Rotate Left X & D Registers Instruction

The operation of ROLXD is:

C<-D15:0<-X15:0<-C

In other words, ROLXD effectively performs a 33-bit rotation of all bits of the carry flag, the 16-bit D-accumulator and the 16-bit X-index register. The C bit from the previous instruction is rotated into the LSB of the X-index register and the MSB of the D-accumulator is rotated into the C bit. All other bits are rotated left, one bit position. ROLXD is an inherent operation. The operation of ROLXD is further shown in Table 6.

TABLE 6

ROLXD

| Address Mode | Syntax | Cycle 1 |
|---|---|---|
| Inherent | ROLXD | C <- D15:0 <- X15:0 <- C |

The only flag affected is C which gets the pre-shifted value of the MSB of the D-accumulator (i.e., C=D15).

The advantage of the new instructions is that it allows for very efficient, low power, and interruptible multiply and divide capability. Further, it has the advantage that the implementation requires very little area on the chip (e.g., silicon area) to provide the multiply and divide routines.

As the multiply and divide routines are performed using a plurality of instructions as opposed to microcode, the routines are interruptible in a manner as described herein. Further, with use of the conditional nature of the instructions, the number of machine cycles to carry out a multiply or divide routine is decreased relative to other firmware implementations.

It will be recognized by one skilled in the art that the instructions and subroutines may be used and/or modified for use with 8-bit processors as well as 16-bit, 4-bit, 32-bit, and 64-bit processors, etc. Further, various different processors may implement such instructions or like instructions in a variety of manners.

The preceding specific embodiments are illustrative of the practice of the invention. It is to be understood, therefore, that other expedients known to those skilled in the art or disclosed herein may be employed without departing from the invention or the scope of the appended claims. For example, the present invention is not limited to use of such microprocessor instructions in a particular implantable medical device such as a pacemaker, but is useful in other devices as well, particularly those in need of low power processing. The present invention is also not limited to the specific detail instructions presented herein, but such functions may be carried out using other like instructions. The present invention further includes within its scope methods of using the multiply and divide routines as well as the particular instructions described hereinabove.

In the claims, means plus function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

What is claimed is:

1. In a medical device, a method of performing a requested routine of at least one of and combinations of multiplication and divisional operations including program suspension that indicates an interrupt command to trigger an interrupt service routine (ISR) subsequent to completing a most recent portion of the requested routine, for the at least one of and combinations of multiplications and divisional operations thereby performing the requested routine by a processor, the method comprising:

providing the processor comprising a CPU interfaced with memory and further including a processor status word register storing an interrupt enable I-bit that may be set or not set, a register storing a conditional bit having a bit state that signifies whether a multiplication or division operation is enabled, a register storing an operand used in a multiplication or division operation, and an accumulator for storing the results of the multiplication and division operations, said CPU capable of performing a CPU normal program operations and an interrupt service routine (ISR) operation;

executing a conditional instruction to add or subtract an operand addressed by the conditional instruction to stored contents of said accumulator and to store the result back in said accumulator if the conditional bit is in a predetermined conditional bit state;

repeating the executed step a predetermined number of times;

providing device operational circuitry for performing a medical device function that generates interrupts including a maskable CPU interrupt, to interrupt the CPU when prescribed medical device functions occur;

suspending the executing step upon receipt of a maskable CPU interrupt if said I-bit in the processor status word register is set;

executing the ISR operation in response to the receipt of the maskable CPU interrupt; and completing said requested routine for the at least one of and combinations of multiplication and divisional operations subsequent to completing said ISR operation.

2. The method according to claim 1 wherein the operation of providing inputs to interrupt the CPU includes the provision of XIRQ and XNMI inputs.

3. The method according to claim 2 wherein said XNMI input is non-maskable.

4. The method according to claim 1 wherein the suspending step includes the steps of suspending CPU normal program operation, saving the program counter, processor status word and a direct page register on a stack and jump to a location of the ISR operation.

5. The method according to claim 1 wherein said operation of executing includes stacking a selected CPU registers and executing instructions corresponding to an interrupt source.

6. The method according to claim 1 wherein XDPOR is implemented to reset the processor to power on reset conditions.

7. The method according to claim 1 wherein said operation of suspending includes sensing a signal leading to an ISR operation to cause CPU normal program operation execution to be discontinued as soon as a currently executing instruction is completed.

8. The method of claim 1, wherein the processor includes a carry flag bit within the processor status word register and an index register, and wherein the step of obtaining the conditional bits includes the step of shifting all bits of the carry flag bit, the accumulator, and the index register right one position so that the least significant bit of the accumulator is shifted to the most significant bit of the index register, the least significant bit of the index register is shifted to the carry flag bit, and the carry flag bit is shifted to the most significant bit of the accumulator, and wherein a predetermined one of the bits of the index register is the conditional bit.

9. The method of claim 8, and further including the step of decoding a shift instruction, and using signals generated from the decoding of the shift instruction to control the shifting step.

10. The method of claim 1, wherein the conditional instruction is a conditional add/subtract instruction, and wherein the executing step further includes subtracting the operand addressed by the conditional instruction from the stored contents of the accumulator if the conditional bit is in a first predetermined state and adding the operand addressed by the conditional instruction with the stored contents of the accumulator if the conditional bit is in a second predetermined state.

11. The method of claim 1, wherein the processor includes a carry flag bit within the processor status word register and an index register, and wherein the step of obtaining the conditional bit includes rotating all bits of the carry flag bit, the accumulator, and the index register left one position such that the carry flag bit is rotated into the least significant bit of the index register, the most significant bit of the index register is rotated into the least significant bit of the accumulator, and the most significant bit of the accumulator is rotated into the carry flag bit, and wherein a predetermined one of the bits of the index register is the conditional bit.

12. The method of claim 11, and further including the step of decoding a rotate instruction, and using signals generated from the decoding of the rotate instruction to control the rotating step.

13. A method of executing at least one of, and combinations of, multiplication and division operations, using a program suspension as an indicator for an interrupt command to trigger an ISR subsequent to completing a most recent portion of a requested routine, for the at least one of and combinations of multiplications and division operations, by a processor of a medical device, the method comprising:

a.) providing the processor comprising a CPU interfaced with a register storing a conditional bit having a bit state that signifies whether a multiplication or division operation is enabled, a register storing a first predetermined operand used in a multiplication or division operation, and an accumulator for storing the results of the multiplication and division operations as a second predetermined operand, said CPU capable of performing a CPU normal program operation and an interrupt service routine (ISR) operation;

b.) executing a conditional instruction whereby said first predetermined operand is added to said second predetermined operand if the conditional bit is in a predetermined state signifying a multiplication operation;

c.) repeating steps a.) and b.) a predetermined number of times;

d.) receiving at least one interrupt signal during the repetition of steps a.) through c.), and in response thereto, completing a currently executing one of the steps a.) and b.);

e.) responding to the at least one interrupt signal; and f.) completing execution of the predetermined number of repetitions of steps a.) through c.) after step e.) is completed.

14. The method according to claim 13 wherein the at least one interrupt signal includes a maskable interrupt signal.

15. The method according to claim 13 wherein the at least one interrupt signal includes a non-maskable interrupt signal.

16. The method according to claim 13 wherein the processor includes a program counter, a processor status word, a page register, and a storage device, and step d.) includes storing the contents of the program counter, the processor status word and the page register on a stack entry in the storage device, and jumping to an address in the storage device to begin execution of an interrupt service routine.

17. The method according to claim 13 wherein step e.) includes executing machine instructions corresponding to a source of the interrupt signal.

18. The method of claim 13, wherein step a.) is performed by the processor executing one of the group of instructions consisting of a shift instruction and a rotate instruction.

19. The method of claim 18 wherein the processor includes a carry flag bit, and an index register, and wherein executing the shift and rotate instructions includes the steps of:
   configuring the carry flag bit, the index register, and the accumulator into a circular shift register;
   shifting all bits in a predetermined direction one bit position; and
   utilizing a predetermined bit within the circular shift register as the conditional bit.

20. The method of claim 13, wherein the first predetermined operand is addressed by the conditional instruction.

21. The method of claim 20, wherein the second predetermined operand is the contents of the accumulator.

22. The method of claim 21, wherein the sum produced during the execution of step b.) is stored back into the accumulator of the processor.

23. The method of claim 13, wherein step b.) further includes the step of subtracting the first predetermined operand from the second predetermined operand if the conditional bit is not in the predetermined state.

24. A processor for use in a medical device including a system to perform interruptible multiplication and division operations, including a program suspension indicator to indicate an interrupt command that triggers an ISR subsequent to completing a most recent portion of a requested routine, for at least one of and combinations of multiplications and division operations comprising:
   an instruction decoder to decode a conditional add instruction and to generate an add control signal in response thereto;
   a storage device to store at least one predetermined conditional bit having either a first or second predetermined state;
   a memory device that stores a first operand to be employed in multiplication and division operations;
   an accumulator that stores the results of the multiplication and division operations as a second operand;
   arithmetic control unit (ALU) logic coupled to the instruction decoder and to the storage device, the ALU logic operable in a multiplication operation in response to generation of the add control signal to obtain said at least one predetermined conditional bit, to add said first and second operands if the at least one predetermined conditional bit is in a first predetermined state, to store the sum of the first and second operands in the accumulator, and to repeat the obtaining of the at least one predetermined conditional bit and the adding and storing of the first and second operands a predetermined number of times;
   interrupt means for generating an interrupt; and
   interrupt logic responsive to an interrupt that allows the ALU to complete the steps of obtaining said at least one predetermined conditional bit and adding and storing the sum of said first and second operands if the at least one predetermined conditional bit is in the first predetermined state and then interrupts the ALU multiplication operation after completion of storing the sum of the first and second operands.

25. The processor of claim 27, and further including an address generation circuit coupled to cause the instruction decoder to decode an instruction that is part of an interrupt service routine after the interruption of the ALU by the interrupt logic.

26. The processor of claim 25, wherein the address generation circuit includes circuits to cause the ALU to resume execution of any uncompleted repetitions of the obtaining of the at least one predetermined conditional bit and any uncompleted repetitions of the adding and storing of the sum of the first and second operands after execution of the interrupt service routine is completed.

27. The processor of claim 26, further including a memory device coupled to the instruction decoder to store the conditional add instruction and to provide the conditional add instruction to the instruction decoder.

28. The processor of claim 27, wherein the address generation circuit includes circuits to cause the first operand to be retrieved from the memory device.

29. The processor claim 24, wherein the instruction decoder decodes a conditional subtract instruction and generates a subtract control signal and the ALU logic is operable in a division operation in response to generation of the subtract control signal to obtain said at least one predetermined conditional bit, to subtract said first operand from said second operand if the at least one predetermined conditional bit is in a second predetermined state, to store the result of the subtraction in the accumulator, and to repeat the obtaining of the at least one predetermined conditional bit and the subtracting of the first and second operands and storing the result a predetermined number of times.

30. The processor claim 29, wherein the interrupt logic responds to an interrupt by allowing the ALU to complete the steps of obtaining said at least one predetermined conditional bit, subtracting said first operand from said second operand, and storing the results in the accumulator if the at least one predetermined conditional bit is in the second predetermined state and then interrupts the ALU division operation after completion of storing the results of the subtraction of the first operand from the second operand.

31. The process of claim 24, wherein the interrupt logic includes programmable means to prevent the ALU from being interrupted.

* * * * *